United States Patent
Alcock et al.

[19]
[11] Patent Number: 5,256,272
[45] Date of Patent: Oct. 26, 1993

[54] ELECTROCHEMICAL SENSOR FOR DETERMINING THE LEVEL OF A CERTAIN METAL IN METALS AND ALLOYS

[76] Inventors: Charles B. Alcock, 310 Runaway Bay, Apt. 3C, Michawaka, Ind. 46545; Baozhen Li, 143 E. Cripe St., South Bend, Ind. 46637

[21] Appl. No.: 848,872
[22] Filed: Mar. 10, 1992
[51] Int. Cl.$^5$ .............................................. G01N 27/26
[52] U.S. Cl. ................................. 204/421; 204/422; 204/423
[58] Field of Search ............... 204/416, 421, 422, 423; 429/33, 191

[56] References Cited

U.S. PATENT DOCUMENTS

| | | | |
|---|---|---|---|
| 4,166,009 | 8/1979 | Fray | 204/422 |
| 4,338,272 | 7/1982 | Pelton et al. | |
| 4,352,869 | 10/1982 | Mellors | 429/191 |
| 4,575,410 | 3/1986 | Neti | 204/422 |
| 4,851,303 | 7/1989 | Madou et al. | 204/426 |

OTHER PUBLICATIONS

"A Flouride-Based Composite Electrolyte", C. B. Alcock, et al., 1990—pp. 245-249.

*Primary Examiner*—John Niebling
*Assistant Examiner*—Bruce F. Bell

[57] ABSTRACT

An electrochemical sensor for determination of the activity of a certain metal in a metal or alloy being tested comprises a solid electrolyte consisting of a solid solution of strontium fluoride and lanthanum fluoride to which is added a dispersed phase of a fluoride of such certain metal, a reference electrode of known concentration of such certain metal placed in contact with one face of the electrolyte, an opposite face of the solid electrolyte being in contact with the metal or alloy being tested, and a device for measuring the chemical potential difference between the reference electrode and the metal or alloy being tested.

7 Claims, 2 Drawing Sheets

ELECTROCHEMICAL SENSOR FOR DETERMINING THE LEVEL OF A CERTAIN METAL IN METALS AND ALLOYS

FIELD OF THE INVENTION

This invention relates to a sensor for measuring the level of a certain metal in metals and alloys, and more particularly for continuously monitoring he level of soluble aluminum in molten zinc.

BACKGROUND OF THE INVENTION

Small amounts of Al are added to molten zinc during continuous galvanizing of steel to control the reaction between the iron of the strip and the zinc in the bath. The aluminum retards the formation of brittle Fe/Zn intermetallic phases on the surface of the strip.

Control of Al in Zn is also important to Zn producers who supply pre-alloyed Al-Zn ingots to the steel galvanizing industry.

Al is added to Zn in specific amounts to produce some Zn/Al casting alloys. The amount of Al will control the properties of the alloy.

In all cases, to determine the Al level, samples are taken from a molten bath, solidified and subsequently analyzed elsewhere by existing analytical techniques. This is a slow process and can cause delays if the analyses are used for process control. Also, the precision of some of the analytical techniques is barely comparable to the analytical accuracy required, especially in the case of galvanizing. In addition, because analytical samples are not always homogenous in terms of the Al concentration, misleading results are often encountered. Local variations in the Al concentration within the analytical sample happen frequently due to the presence of Al-bearing second phase particles and to aluminum segregation during solidification.

SUMMARY OF THE INVENTION

It is the primary object of the present invention to provide an electrochemical sensor to continuously monitor the active content of a certain metal in a metal or alloy, such as the active content of aluminum in liquid zinc. Such a sensing device would be free of sampling problems and would provide means of continuously monitoring the aluminum concentration in the zinc bath. Both of these features offer significant advantages over the present monitoring practice.

The electrochemical sensor in accordance with the present invention comprises a solid electrolyte consisting of a solid solution of strontium fluoride ($SrF_2$) and lanthanum fluoride ($LaF_3$) to which is added a dispersed phase of a fluoride of the metal the activity of which is to be determined, a reference electrode having a known concentration of the metal the activity of which is to be determined placed in contact with one face of the solid electrolyte, an opposite face of the solid electrolyte being in contact with the metal being tested, and means for measuring the electromotive force between the reference electrode and the metal being tested.

The electrochemical sensor is preferably used to measure the activity of aluminum in molten zinc. In such a case, the dispersed phase is aluminum fluoride and the reference electrode made of pure aluminum or of an aluminum alloy of a given aluminum activity.

The solid electrolyte composition is preferably 70% mol. $SrF_2$ and 30% mol. $LaF_3$ to which is added 2–8% mol. $AlF_3$.

The invention will now be disclosed, by way of example, with reference to the accompanying drawings in which:

DETAILED DESCRIPTION OF THE PREFERRED EMBODIMENTS

A fluoride-based composite electrolyte for electrochemical sensors has been previously developed by the Center for Sensor Materials of the University of Notre Dame (C. B. Alcock and Baozhen Li, A Fluoride-Based Composite Electrolyte, Solid State Ionics, 39, (1990) 245–249). It is a fluorine ion conductor and has been used as the base electrolyte material for oxygen, sulfur, carbon and hydrogen sensing through dispersing a small amount of an appropriate second phase in the electrolyte. Applicants have now surprisingly found, in accordance with the present invention, that the above base electrolyte material may also be used for sensing metal activity in liquid and solid metal and alloy systems. For the determination of Al activity in liquid Zn, a certain amount of aluminum fluoride ($AlF_3$) is added to the $SrF_2$-$LaF_3$ electrolyte.

The electrochemical cell is described as

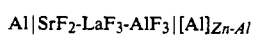
$$Al\,|\,SrF_2\text{-}LaF_3\text{-}AlF_3\,|\,[Al]_{Zn\text{-}Al}$$

where pure Al (or a Zn-Al alloy of known Al concentration) is the reference electrode and the molten Zn-Al alloy is the working electrode. The electrode processes are:

left half cell

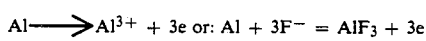
$$Al \longrightarrow Al^{3+} + 3e \text{ or: } Al + 3F^- = AlF_3 + 3e$$

right half cell

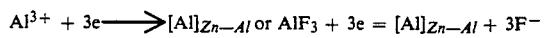
$$Al^{3+} + 3e \longrightarrow [Al]_{Zn-Al} \text{ or } AlF_3 + 3e = [Al]_{Zn-Al} + 3F^-$$

the overall cell reaction is

$$Al \longrightarrow [Al]_{Zn-Al}$$

Therefore this is an aluminum concentration cell. The relationship between the cell EMF and the aluminum activity in the Zn-Al alloy can be described through the Nernst equation:

$$E = RT/nF \ln a_{Al}$$

where E is the cell EMF, n is the number of electrons involved in the cell reaction, $a_{Al}$ is the aluminum activity in the Zn-Al alloy, R is the gas constant, T is the temperature in Kelvins, F is the faraday constant.

The measured EMF may be displayed on a meter for example, or on any suitable display instrument, or alternatively, it may be recorded either electronically or in the form of a line or a trace as a function of time.

Figure 1:
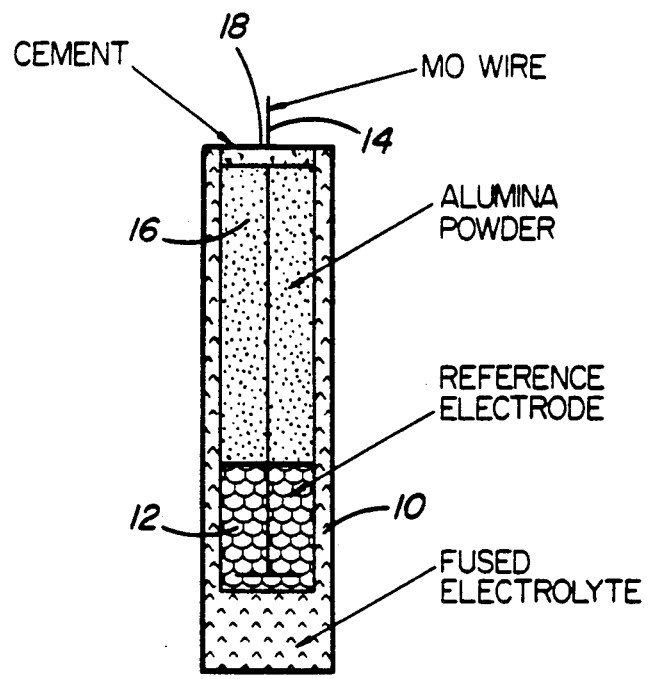
FIG. 1 is a cross-section of an embodiment of a probe for monitoring the active Al content in liquid Zn.

Referring to FIG. 1, there is shown a probe in the shape of a tube 10 which is closed at one end and is made from an electrolyte material having the composition (0.7 $SrF_2$-0.3 $LaF_3$)-(2-8% $AlF_3$)). Inside the tube is placed a reference electrode 12 made of pure aluminum or an aluminum alloy of known aluminum concentration with a suitable contact 14, such as a Mo wire, extending out of the tube for connection to a suitable EMF measuring instrument. These elements are supported in the sensor tube with alumina powder 16 and the assembly is sealed with cement 18.

The electrolyte tube is preferably made by slip casting following generally the technique disclosed in U.S. Pat. No. 4,338,272. Adjustments have to be made, however, for casting the fluoride tube. In making the tube, very fine alumina powder (−325 mesh) is compacted to make molds, and the electrolyte powder (about −150 mesh) is mixed with absolute (ethyl) alcohol in the powder: solvent ratio of 1:4 by weight to make suspensions. In order to achieve a good quality of suspension, which is crucial to the tube quality, the powder size and powder to solvent ratio are very important. After casting the suspension into the mold, it is kept at room temperature for 36 to 48 hours to allow the primary drying of the tube. The green tube can be taken out by carefully removing the mold powders. Then, the tube is heated to 350°–400° C. in argon for a few hours to completely remove the alcohol, and slowly to about 1000° C. for a few hours for the final sintering.

Figure 2:
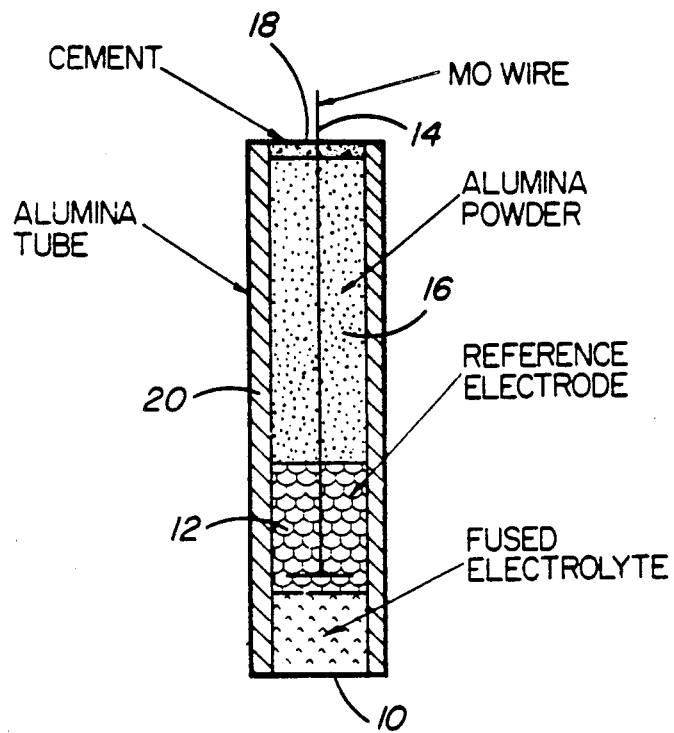
FIG. 2 is a cross-section of an alternative probe.

The electrolyte material could also be fused into the end of an alumina tube 20 as shown in FIG. 2. After solidification, the electrolyte would seal one end of the tube. The rest of the probe would be similar to that shown in FIG. 1.

Figure 3:
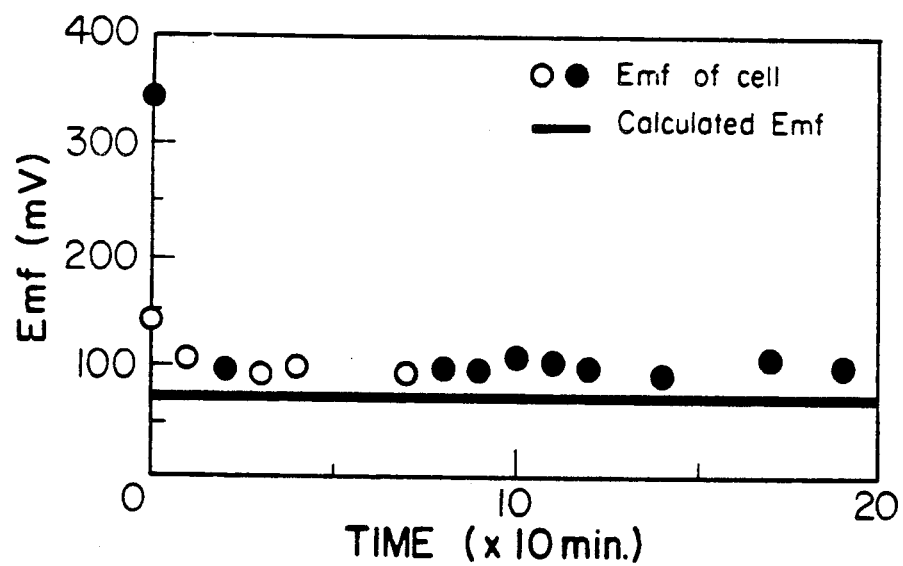
FIG. 3 is a graph showing the variation of probe EMF with time.

The probe has been tested in laboratory scale Zn/Al baths. FIG. 3 shows that for a nominal Zn-1.6 wt % Al alloy, the aluminum activity was obtained as about 0.012 (1.2 mol % or 0.5 wt %) in the temperature range 430–500 Deg. C. A stable EMF can be measured for hours, and can be reproduced to within ±10 mV. At this high Al concentration the Zn/Al alloy may not be treated as an ideal solution and the assumption that the activity equals the concentration may not be true, and hence the activity coefficient of Al is not unity. Therefore there is expected to be some difference between the concentration by chemical analysis and the activity measured by the electrochemical probe.

Even though the sensor is primarily for the aluminum determination in molten zinc, it could be applied to the determination of other metals in many liquid and solid metal and alloy systems.

We claim:

1. An electrochemical sensor for determination of the activity of a certain metal contained in a metal or alloy being tested comprising:

a solid electrolyte consisting of a solid solution of about 70% strontium fluoride and about 30% mol. lanthanum fluoride to which is added a dispersed phase of a fluoride of said certain metal, a reference electrode of known concentration of said certain metal having an activity to be determined placed in contact with one face of said electrolyte, an opposite face of said solid electrolyte being in contact with the metal or alloy being tested, and means for measuring the chemical potential difference between said reference electrode and said metal or alloy being tested.

2. An electrochemical sensor as defined in claim 1, wherein said certain metal is Al and wherein the metal or alloy being tested is molten zinc.

3. An electrochemical sensor as defined in claim 2, wherein the dispersed phase is 2–8% mol. $AlF_3$.

4. An electrochemical sensor as defined in claim 2, wherein the reference electrode is pure aluminum or an aluminum alloy of a given aluminum activity.

5. An electrochemical sensor as defined in claim 1, wherein the means for measuring the electromotive force is a meter or any suitable display or recording instrument.

6. An electrochemical sensor as defined in claim 1, wherein the solid electrolyte is in the shape of a tube which is closed at one end and wherein the reference electrode is placed at the bottom of the tube.

7. An electrochemical sensor as defined in claim 1, wherein the solid electrolyte is melted and solidified at one end of an alumina tube and wherein the reference electrode is placed in the alumina tube in contact with the solid electrolyte.

* * * * *